(12) United States Patent
Bradley et al.

(10) Patent No.: US 7,375,215 B2
(45) Date of Patent: May 20, 2008

(54) COMPOUNDS FOR PDT

(75) Inventors: Paul Bradley, Leicestershire (GB);
Mehar Manku, Cumbria (GB)

(73) Assignee: Bioscience Technology Investment Holdings Limited, F.T. Labuan (MY)

( * ) Notice: Subject to any disclaimer, the term of this patent is extended or adjusted under 35 U.S.C. 154(b) by 95 days.

(21) Appl. No.: 10/221,218

(22) PCT Filed: Mar. 8, 2001

(86) PCT No.: PCT/GB01/01010

§ 371 (c)(1),
(2), (4) Date: Aug. 8, 2005

(87) PCT Pub. No.: WO01/66550

PCT Pub. Date: Sep. 13, 2001

(65) Prior Publication Data

US 2006/0040912 A1    Feb. 23, 2006

(30) Foreign Application Priority Data

Mar. 10, 2000 (GB) .................................. 0005855.2

(51) Int. Cl.
 C07D 487/22    (2006.01)
 C07D 47/00     (2006.01)
 C08G 18/08     (2006.01)
 A01N 55/02     (2006.01)
 A61K 31/409    (2006.01)
 A61K 31/555    (2006.01)

(52) U.S. Cl. .................... 540/145; 525/460; 514/185; 514/410; 514/184; 514/186; 514/187; 514/188; 514/189; 514/190

(58) Field of Classification Search ................ 540/145
See application file for complete search history.

(56) References Cited

U.S. PATENT DOCUMENTS

2002/0155999 A1 * 10/2002 Han ............................ 514/8

FOREIGN PATENT DOCUMENTS

| WO | WO 91 18630 A | 12/1991 |
|---|---|---|
| WO | WO 95 29915 A | 11/1995 |
| WO | WO 9529915 | * 11/1995 |
| WO | WO 98 01156 A | 1/1998 |
| WO | WO 98 37057 A | 8/1998 |

OTHER PUBLICATIONS ("Cancer form Online Medical Dictionary," http://cancerweb.ncl.ac.uk/cgi-bin/omd?/query=cancer, accessed Jun. 12, 2007.*
Sax and Lewis. Hawley's Condensed Chemical Dictionary, Eleventh Edition. Van Nostrand Reinhold: 1987, New York, p. 21.*
"MeSH Result", http://www.ncbi.nlm.nih.gov/sites/entrez?Db=mesh&Cmd=ShowDetailView&TermToSearch=1000067&ordinalpos=1&itool=EntrezSystem2.PEntrez.Mesh.Mesh_ResultsPanel.Mesh_RVFull, accessed Jun. 25, 2007.*

* cited by examiner

*Primary Examiner*—James O. Wilson
*Assistant Examiner*—Noble Jarrell (57) ABSTRACT

A tetrakis(hydroxyphenyl)chlorin, bacteriochlorin or isobacteriochlorin, derivatised at one or more of the hydroxy groups by addition reaction with a diisocyanate, diisothiocyanate or isocyanate-isothiocyanate at one isocyanate or isothiocyanate group thereof, the other isocyanate or isothiocyanate group being itself derivatised by addition reaction with the hydroxy group of an w-alkylated or acylated poly(alkylene oxide) or to a hydroxy group of a link residue itself carrying a residue of such poly(alkylene oxide).

1 Claim, 4 Drawing Sheets

COMPOUNDS FOR PDT

This application is the US national phase of international application PCT/GB01/01010 filed 8 Mar. 2001, which designated the US.

FIELD OF INVENTION

The invention relates to poly(alkylene oxide) substituted photosensitising compounds and to their use in photodynamic therapy of cancerous and other diseased tissues.

BACKGROUND

Photodynamic therapy (PDT) involves the administration of a photosensitising agent for localisation in target diseased tissue followed by irradiation of the target tissue containing the compound with light of a specific and appropriate wavelength. The resulting photoactivated compound, in the presence of oxygen, leads to necrosis of the tissue.

The success of this modality is dependent on administration of a compound that is selectively retained in tumour tissue as compared to normal tissue. Thus, on irradiation of the tumour with light of the photoactivating wavelength, the amount of damage caused by necrosis is proportionately higher than that in normal tissue. However, some normal tissue damage typically occurs and one specific side effect seen with the use of many photosensitisers is redness and swelling of the skin on subsequent exposure to normal lighting levels and particularly sunlight. Such side effects are minimised by keeping the patients in subdued light for a prolonged period after treatment, consequently restricting their quality of life. A more efficient delivery of the photosensitiser into tumour tissue, thus providing a much higher tumour to normal tissue ratio of drug concentration could dramatically reduce the potential for skin side effects with this treatment.

A group of photosensitising agents have previously been the subject of patents EP 0 337 601 and U.S. Pat. No. 4,992,257. These compounds are dihydroporphyrins (chlorins) (1) and the corresponding tetrahydroporphyrins (bacteriochlorins) (2) and (3) of the formulae:

(1)

(2)

(3)

wherein each n=1 to 3 and each substituent, R, the same or different, is a hydroxyl (—OH) group, each itself free or substituted with an alkyl or acyl group. Salts, internal salts, metal complexes or hydrates or other solvates of the compounds are also covered.

The above formulae, it will be appreciated, represent particular tautomers among various possibilities including chlorins as shown below (represented without meso Phenyl groups):

(4)

(5)

(6)

(7)

bacterichlorins (8)

(9)

and isobacteriochlorins (10)

(11)

The invention covers all tautomers of the above compounds and is not limited to those shown in diagrams.

Published Proposals

Modification of compounds by PEGylation, that is the direct or indirect attachment of polyethylene glycol chains (PEG), and in principle other poly(alkylene oxide) chains, is known to introduce useful properties. PEG is non-toxic, imparts good water solubility to drug molecules and alters the biodistribution, which can result in a favourable pharmacokinetic profile. The general topic of polyether substituted anti-tumour agents is described in DKFZ's specification PCT EP 91/00992 (WO 91/18630). No particular attention is given to the selection of the linkage between the polyether chain and the anti-tumour agent, the only example disclosed being a triazine introduced by initial activation of the polyether with cyanuric chloride. More recently, DKFZ have described a method for the production of chlorins and bacteriochlorins containing a polyether (WO 98/01156). The method involves initial attachment of the polyether to the porphyrin with subsequent reduction to the corresponding chlorins and bacteriochlorins. Again, no particular attention is given to the nature of the linkage between the polyether and the anti-tumour agent, the only example disclosed being an amide link.

PEGylation of compounds (1), (2) and (3) via triazine, ether and ester linkages has been previously reported by us in PCT GB 95/00998 (WO 95/29915). However, lability of the ester linkages and significant difficulties in the scale up of the triazine and ether linked moieties severely limits the practical utility of these compounds.

Enzon have also reported polyether compositions containing isocyanate and/or isothiocyanate groups for covalent attachment to bioeffecting substances such as peptides or chemotherapeutics (WO 94/04193). However, in relation to isocyanates and isothiocyanates, coverage is directed to compounds in which bioeffecting substances are attached to both ends of the polyether chain.

Outside the PDT field, hexane-1,6-diisocyanate has been used to link PEG to atropine (Zalipsky et al, Eur. Polym. J. 1983, 19(12), 1177-1183) and to 5-fluorouracil (Ouchi et al, Drug Design and Discovery 1992, 9, 93-105). Bayer (U.S. Pat. No. 4,684,728) have reported a process for improving the solubility in water of a sparingly soluble biologically active compound by reaction to form a derivative carrying the active moiety, a linking group such as an optionally substituted diisocyanate group and a polyether chain. No mention is made of any benefit to the therapeutic profile of such compounds other than the ease of formulation and administration of a water soluble compound.

Discussion of Present Work

Advances in photodynamic therapy for clinical disease treatment, particularly cancer, depend on developing improved photosensitisers. The desired characteristics of an ideal photosensitiser include selective diseased tissue localisation, activation at long wavelengths so that maximum depth of tissue penetration is shown, and high efficiency as sensitisers. From a formulation and administration point of view, water solubility is also a beneficial attribute.

Photodynamic therapy is a dual therapy, which consists of the combined action of photosensitiser and light. In clinical practice the drug is first administered, and then activated by light some time later. The time period between administering the drug and applying the light is called the drug-light interval. It is desirable to apply light at a time when the photosensitiser has accumulated maximally in the target tissue and has been eliminated from the normal surrounding tissue. The principal factor determining the drug-light interval is the drug pharmacokinetic profile which itself varies between every tissue. The drug-light interval has to be suitable for clinical practice. From a clinical standpoint, pharmacokinetics which give a maximum drug concentration in a tumour as soon as possible, for example from a few hours to at most 3 days, together with rapid elimination from the body thereafter, would be ideal. This would allow flexibility in scheduling treatment.

In European Patent Specification 0 337 601 (U.S. Pat. No. 4,992,257), the applicants disclose compounds with many of the desired characteristics, particularly an extremely high photo efficiency, that is to say the ability to generate free radical species such as singlet oxygen through the absorption of light. The long absorption wavelengths of the molecules, e.g. at 652 nm and 734 nm, penetrates tissue efficiently and thus the sensitisers can be used to treat deep tumours.

However, the disclosed compounds do not fulfil all the requirements equally well. A residual disadvantage is the degree of normal tissue photosensitivity, particularly of the skin, that occurs following administration of the sensitiser. This arises from unwanted deposition of the sensitiser in the skin and other normal tissue and is a consequence of imperfect tumour targeting by the drug. The skin photosensitivity can last up to 4 weeks depending on the drug dose administered. At the usual clinical dose of 0.15 mg $kg^{-1}$ skin sensitivity of, for example, m-THPC (a tetraphenyl chlorin derivative in which each phenyl group carries a m-hydroxy group) lasts for 2-3 weeks. This limits the patient's freedom and is an undesirable restriction.

We have sought ways of overcoming normal tissue photosensitivity, particularly of the skin, by converting m-THPC to a polyethylene glycol derivative. This 'PEGylation' profoundly alters the bodily distribution in a favourable way by increasing tumour targeting, and at the same time reducing uptake to the skin. The distribution of the compound is altered by PEGylation, due to hydrogen bonding of water to oxygen on the polyethylene glycol chains when the compound is injected into the blood. A 'water envelope' forms around the photosensitiser and prevents the compound sticking to the endothelium of blood vessel walls and in turn passing into the surrounding tissue including the skin. This favours uptake to the tumour through the enhanced permeability and retention (EPR) effect. Tumours have a disturbed vasculature and lymphatic drainage, leading to increased accumulation of substances such as drugs in the tumour compared to normal tissue (R. Duncan and F. Spreafico, Clin. Pharmacokinet. 1994, 27, 290-306). This effect can be enhanced with higher molecular weight compounds. The net effect of PEGylation is that the compound is favourably redirected from the skin and other normal tissues towards the tumour, thus reducing the degree of skin sensitivity.

It has been confirmed experimentally, for example, that PEGylation can produce a favourable tissue re-distribution. This was shown in a mouse experimental model in which an outstanding difference between muscle and tumour photosensitivity during PDT was found for the triazine-linked derivative (Grahn et al., Proc. SPE 1997, 3191, 180-6). Three days after the PEGylated m-THPC was administered it was found that the muscle was no longer photosensitive, while the tumour retained its maximum sensitivity to light for at least 15 days after drug administration. This presented ample time for tumour-selective treatment, but did indicate the less desirable characteristic of tumour persistence with this derivative.

Other work previously performed with triazine-linked PEG derivatives [applicants PCT Patent specification WO 95/29915, (PCT/GB95/00998)] confirmed that the pharmacokinetics with the triazine linkage were rather too prolonged for routine clinical use. In particular, excretion from the liver was very slow indeed, which is undesirable pharmaceutically.

An alternative linker to the triazine molecule was sought, including a glycidic ether with amino PEG and also an hexylbiscarbamate linker. The PEGylated derivatives of m-THPC with triazine and carbamate links have very different and unexpected pharmacokinetics to each other and m-THPC. The triazine-linked compound (SPC 0038B) is excreted from the liver more slowly than m-THPC, while the carbamate derivative (SPC 0172) is excreted in a comparable period to m-THPC. The solubilities of the compounds, and hence ease of pharmaceutical preparation, were enhanced to levels of up to 52 mg/mL in water, compared to m-THPC, which is insoluble in aqueous solvents.

The linker group should provide a stable point of PEG attachment, permitting reasonable in vivo circulation and should be available via a practical and robust synthesis. It should not, however, affect the PDT efficiency of the drug molecule. The method of Zalipsky was modified and utilised for a two step synthesis from the chlorin and bacteriochlorin molecules to their PEGylated derivatives. Analysis of these compounds using gel permeation chromatography (GPC) allowed separation of lesser PEGylated forms, but high performance liquid chromatography (HPLC) proved superior with separation between the peaks of 0.8 min. Reaction products were also analysed by UV/Visible spectroscopy, which gave a quantitative measurement of molecular weight (mw) using the formula:

Apparent $mw = mw$ (chlorin) $\times A_{(1\%,\ 1\ cm)}$ (chlorin)$/A_{(1\%,\ 1\ cm)}$ (PEG chlorin).

The applicants work has thus built on previous work in trying to develop an ideal sensitiser. Unpredictably, the carbamate-linked polyethylene glycol derivatives have an excellent and preferred pharmacokinetic profile from a clinical point of view and exhibit less potential to cause cutaneous photosensitivity. Furthermore, studies in Balb/c mice bearing colo26, a murine colorectal cancer, show that the photodynamic effect of the carbamate-linked derivative in tumour is maximum at 2 days and that it has the same PDT activity as m-THPC itself This is considerably more active than the triazine-linked compound. Thus overall, the PEGylated carbamate-linked compound appears to add new features, which enhance the desired characteristics of the sensitiser.

The Invention

The present invention summarised below and set out in the claims thus concerns the derivatisation or partial derivatisation of the phenolic groups of compounds of formulae (1), (2) and (3) with poly(alkylene oxides) using a carbamate or thiocarbamate link:

(X═O, S) formed by addition reaction of the compounds with an isocyanate (—N═C═O) or isothiocyanate (—N═C═S) group of a diisocyanate, diisothiocyanate or an isocyanate-isothiocyanate, the poly(alkylene oxide) chain being attached directly or indirectly by addition at the other group and its terminal hydroxyl group being etherified or esterified with for example a $C_{1-12}$ alkyl or acyl group of which methyl is the most preferred.

The reactions, which may be carried out in any convenient order, result in compounds of formulae:

(12)

(13)

-continued (14)

and imino-tautomers thereof wherein n=1 to 3 and R' may be the same or different, is a hydroxyl (—OH) group, each itself free or substituted with an alkyl or acyl group, but in at least one, preferably more than one instance is as follows:

(15)

where:
(i) each X, the same or different, is O, S;
(ii) Y is O (carbamate or thiocarbamate link);
(iii) A is a hydrocarbon group containing 2 to 40 carbon atoms, preferably 4 to 20 carbon atoms and very preferably 6 carbon atoms. This group may be branched or unbranched, cyclic or acyclic, saturated or unsaturated, aliphatic or aromatic;
(iv) B is an optional group $((CH_2)_p-O)_q$ where p=1 to 4; q=0,1;
(v) D is a poly(alkylene oxide), preferably polyethylene glycol, with an average molecular weight of at least 200 and not more than 40,000, preferably 750 to 20,000 and very preferably 2,000 to 5,000 Da;
(vi) E is an alkyl or acyl group containing 1 to 12 carbon atoms, preferably a methyl group.

In any of the above compounds derivatives such as salts with mineral acids (e.g. hydrochlorides, sulphates), internal salts, metal complexes (e.g. with Zn, Ga), or hydrates and other solvates may be formed.

Suitable diisocyanates include butane-1,4-diisocyanate, hexane-1,6-diisocyanate, octane-1,8-diisocyanate, dodecane-1,1 2-iisocyanate, 2-methylpentane-1,5-diisocyanate, toluene-2,4-diisocyanate, toluene-2,6-diisocyanate, cyclohexane-trans-1,4diisocyanate, dicyclohexylmethane-4,4'-diisocyanate, diphenylmethane-3,4'-diisocyanate, xylene diisocyanate and 2,4,4-trimethylhexylmethylene diisocyanate. Corresponding diisothiocyanates and isocyanate-isothiocyanates are also appropriate. The most preferred linker is hexane-1,6-diisocyanate.

Chemistry

Compounds of types (12), (13) and (14) may be prepared in a two step process.
(i) activation of poly(alkylene oxide) by reaction with a diisocyanate, diisothiocyanate or an isocyanate-isothiocyanate (e.g. hexane-1,6-diisocyanate) in a suitable inert, anhydrous solvent (e.g. toluene) with or without a catalyst (e.g. dibutyl tin dilaurate), with or without a tertiary organic base (e.g. triethylamine) at a temperature between 0 and 110° C.
(ii) coupling of the activated poly(alkylene oxide) to the reduced porphyrin in a suitable inert solvent (e.g. toluene) with or without a catalyst (e.g. dibutyl tin dilaurate), with or without a tertiary organic base (e.g. triethylamine) at a temperature between 0 and 110° C.

Synthesis of compounds may also be achieved by reversing the order of the steps, namely activation of the reduced porphyrin by reaction with the diisocyanate, diisothiocyanate or isocyanate-isothiocyanate followed by coupling with the poly(alkylene oxide). However, the former approach is preferred.

Routes of Administrations

By parenteral or any other suitable route in per se known manner.

Pharmaceutical Presentations

Any suitable presentation as known in the field, including, but not limited to:
i) injectable solution
ii) freeze dried powder for reconstitution and injection
iii) infusion solution for addition to saline or other vehicle
iv) tablet or capsule for oral administration.

PREPARATIVE EXAMPLES

Example 1

7,8-Dihydro-5,10,15,20-tetrakis(3-hydroxyphenyl)porphyrin derivatised with ω-methoxy polyethylene glycol (average MW=2000) via biscarbamate linkages derived from hexane-1,6-diisocyanate.

[Compound (12); n=1: meta substitution on all aryl groups; X=O; A=$(CH_2)_6$; Y=O; q=0; D=PEG (average MW=2000); E=$CH_3$]

Part 1: Preparation of Activated mPEG (ω-methoxy Polyethylene Glycol)

A solution of mPEG (average MW=2000, 40 g) in toluene was dried azeotropically for 4 h and added dropwise over a 2 h period to a mixture of anhydrous toluene (100 mL), hexane-1,6-diisocyanate (16.2 mL) and dibutyl tin dilaurate (0.5 mL). After standing overnight under anhydrous conditions, the product was precipitated by the addition of hexane (200 mL). The solid was collected by filtration, reprecipitated from toluene/hexane and dried under vacuum. This yielded the product as a white powder (38 g). Analysis by non-aqueous titration gave an isocyanate assay of 95% of theory. Molecular weight as determined by titration of NCO groups: mPEG$_{2000}$-hexylcarbamateisocyanate 2160 (requires 2168). IR (nujol, cm$^{-1}$) 3300 (NH); 2250 (NCO); 1715, 1535 (HN—COO); 1110 ($CH_2OCH_2$); Aδ$_H$ (CCl$_4$) 1.3-1.6 (m, $CH_2$), 3.6 (s, $OCH_2$). This material was used immediately in the second part of the synthesis.

Part 2: Coupling of Activated mPEG to m-THPC

A mixture of 7,8-dihydro-5,10,15,20-tetrakis(3-hydroxyphenyl)porphyrin (300 mg) and activated mPEG (as prepared in Part 1) (8.95 g) in anhydrous toluene was stirred overnight under nitrogen at 30-60° C. HPLC analysis on an aliquot indicated >95% tetraPEGylation. The product was precipitated by the addition of hexane to the stirred contents at room temperature. The solid was collected by filtration, washed with hexane and dried under vacuum The product was then purified by reverse phase chromatography, eluting with methanol/water. After removal of the methanol under reduced pressure, the solution was freeze dried to yield the product as a dark brown solid.

Example 2

7,8,17,18-Tetrahydro-5,10,15,20-tetrakis(3-hydroxyphenyl)porphyrin derivatised with ω-methoxy poly(ethylene glycol) (average MW=2000) via bis carbamate linkages derived from hexane-1,6-diisocyanate.

[Compound (13); n=1; meta substitution on all aryl groups; X=O; A=(CH$_2$)$_6$; Y=O; q=0; D=PEG (average MW=2000); E=CH$_3$]

By replacing 7,8-dihydro-5,10,15,20-tetrakis(3-hydroxyphenyl)porphyrin with 7,8,17,18-tetrahydro-5,10,15,20-tetrakis(3-hydroxyphenyl)porphyrin and toluene with 1,4-dioxan as solvent in Example 1, Part 2, the title compound was prepared as a brown powder.

Example 3

7,8-Dihydro-5,10,15,20-tetrakis(3-hydroxyphenyl)porphyrin derivatised with ω-methoxy poly(ethylene glycol) (average MW=5000) via bis carbamate linkages derived from hexane-1,6-diisocyanate.

[Compound (12); n=1; meta substitution on all aryl groups; X=O; A=(CH$_2$)$_6$; Y=O; q=0; D=PEG (average MW=5000); E=CH$_3$]

By replacing mPEG (average MW=2000) with mPEG (average MW=5000) in Example 1, Part 1, [Molecular weight as determined by titration of NCO groups: mPEG$_{5000}$-hexylcarbamateisocyanate 4944 (requires 5168)] the title compound was prepared as a brown powder.

Example 4

7,8,17,18-Tetrahydro-5,10,15,20-tetrakis(3-hydroxyphenyl)porphyrin derivatised with ω-methoxy poly(ethylene glycol) (average MW=5000) via bis carbamate linkages derived from hexane-1,6diisocyanate.

[Compound (13); n=1; meta substitution on all aryl groups; X=O; A=(CH$_2$)$_6$; Y=O; q=0; D=PEG (average MW=5000); E=CH$_3$]

By replacing mPEG (average MW=2000) with mPEG (average MW=5000) in Example 1, Part 1 and 7,8-dihydro-5, 10,15,20-tetrakis(3-hydroxyphenyl)porphyrin with 7,8, 17,18-tetrahydro-5,10,15,20-tetrakis(3-hydroxyphenyl)porphyrin in Example 1, Part 2, the title compound was prepared as a brown powder.

Biology

In the following account of work done:

SPC 0172 is carbamate-linked PEG$_{2000}$ m-THPC, compound name tetrakis (6'-(methoxy PEG 2000 carbamate)1'-isocyanate hexamethylene) derivative of 7,8dihydro-5,10, 15,20-tetrakis(3-hydroxyphenyl)porphyrin. This compound is shown in example 1.

SPC 0038B is a corresponding triazine compound, tetrakis (ω-methoxypolyethylene glycol [MW=2000] triazine of 7,8-dihydro-5,10,15,20-tetrakis(3-hydroxyphenyl)porphyrin.

m-THPC is temoporfin or 7,8-dihydro-5,10,15,20-tetrakis (3-hydroxyphenyl)porphyrin, the basis of SPC 0172 and SPC 0038B.

Spectroscopic Properties of SPC 0172

Figure 1:
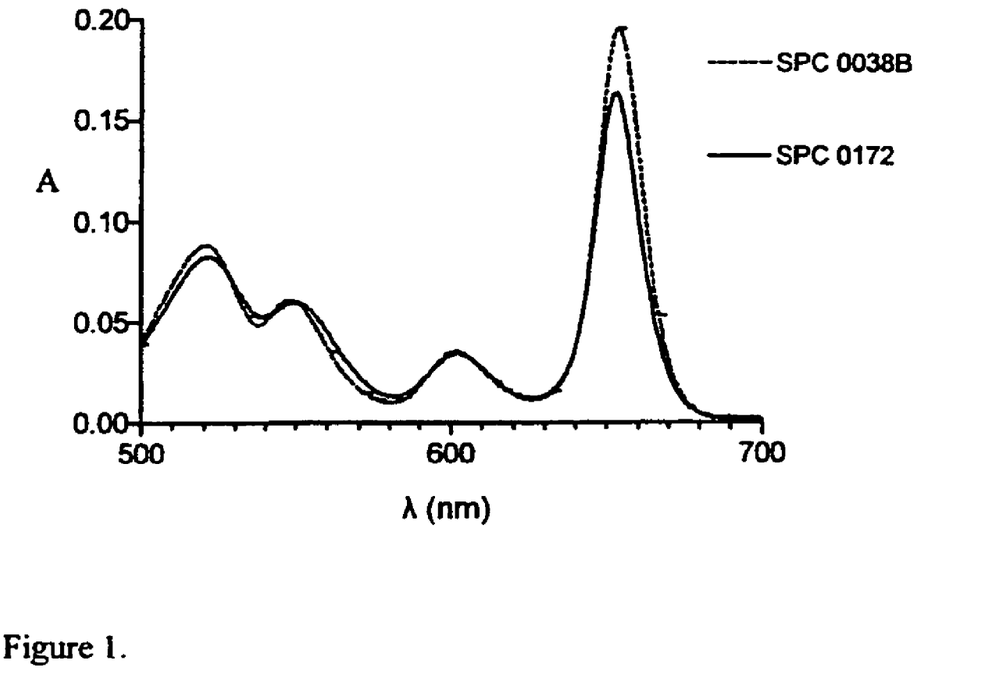

SPC 0172 has a very similar absorption spectrum to that of SPC 0038B which in turn was similar to that of m-THPC (absorption peaks for m-THPC in the 500-700 nm range at 516, 542, 594 and 650 nm). FIG. 1 (Absorbance, A against wavelength, λ) shows the UV-visible absorbance spectra of SPC 0172 and SPC 0038B in 0.25 µM aqueous solution measured using a Hitachi U3000 spectrophotometer. SPC 0172 has a somewhat lower molar extinction coefficient at the red peak than does m-THPC (ca 22,000 L mol$^{-1}$ cm$^{-1}$ compared to ca 30,000 L mol$^{-1}$ cm$^{-1}$).

The fluorescence emission spectrum in ethanol of SPC 0172 is very similar to those of SPC 0038B and m-THPC in the same solvent. All three compounds show a fluorescence emission peak between 655-660 nm when excited by light in the Soret band region (405 nm). m-THPC fluorescence is severely quenched in aqueous solution owing to the formation of aggregates. Both SPC 0038B and SPC 0172 fluoresce more weakly in aqueous solution than in ethanol (47% and 36% respectively) indicating that some aggregation or other conformational change takes place when they are dissolved in water. Both the PEGylated photosensitisers exhibit greatly improved solubility in water (at least 50 mg/ml) compared to m-THPC, which is insoluble.

Uptake by Tumour Cells in Culture

Colo26 mouse colorectal tumour cells were grown in culture using standard methods. Confluent monolayers of the cells kept at 37° C. in the dark were exposed to 1.5 µM m-THPC, SPC 0038B or SPC 0172 added to the incubation medium for periods of between 3 and 72 hours. At the end of the set time period, the culture medium containing the added photosensitiser was removed and the cells washed with cold phosphate buffered saline. The cells were freed from the culture flask by treatment with trypsin solution. The viable cell count was determined using a standard haemocytometer and the photosensitiser extracted from the cells by treatment with methanol:DMSO (4:1, v:v). Cell extracts were frozen in liquid nitrogen and stored at −70° C. for later analysis. The photosensitiser content of the cell extract was determined by direct fluorescence using standard curves of photosensitiser and correcting for extraction efficiency from the cell suspension.

Figure 2:
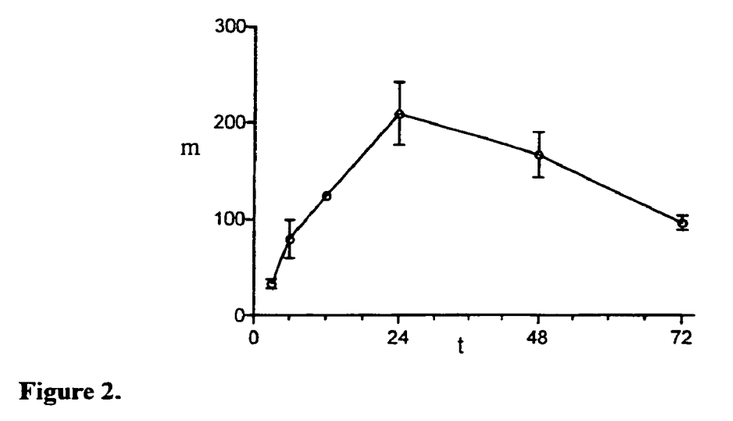
Figure 3:
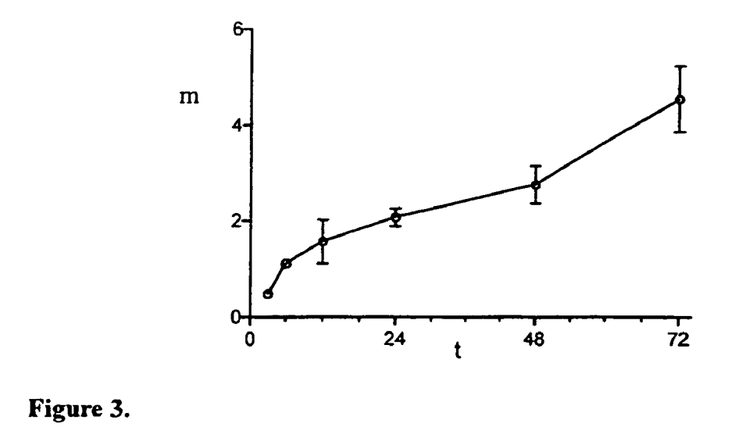
Figure 4:
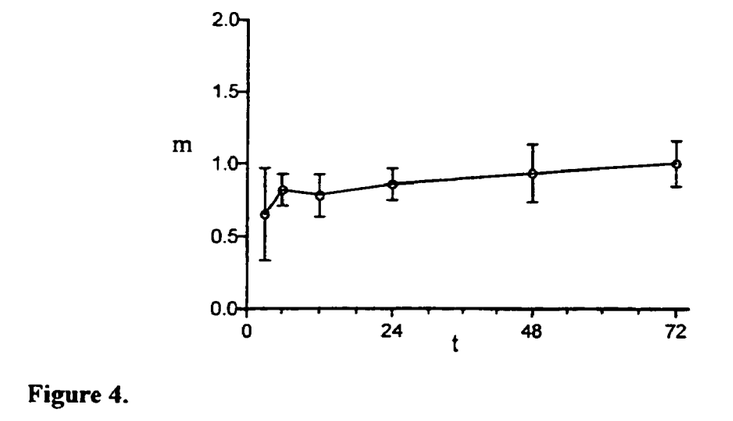

The uptake of the three photosensitisers is shown in FIG. 2 temoporfin uptake by tumour cells in culture, FIG. 3 SPC0172 uptake by tumour cells in culture and FIG. 4 SPC0038B uptake by tumour cells in culture, all at 37° C. (millions of molecules per cell, m against time t (hours)). The amount of photosensitiser is expressed as the number of molecules of photosensitiser (in millions) present within a single cell at each time point The data in FIGS. 2 to 4 represents the mean value obtained from two experiments and the bars represent the range. The uptake of m-THPC is rapid, reaching a peak around 24 hours after which the photosensitiser content of the cells declines. The uptake of SPC 0038B, in contrast is very slow, with a barely detectable increase in cell drug concentration at 72 hours compared with 3 hours of incubation. After 72 hours the cell photosensitiser content is about a factor of 100 less than that of m-THPC. The uptake of SPC 0172 shows the same slower uptake as does SPC 0038B, uptake being relatively linear up to the final measurement point at 72 hours of incubation. However, the amount of photosensitiser taken up is greater. After 72 hours of incubation there is about 5 times as much SPC 0172 in each cell as SPC 0038B, but again this is much less than the peak cellular m-THPC content.

The mechanism of photosensitiser uptake by cells remains a subject of study. In the case of small hydrophobic sensitisers such as m-THPC, which are generally presented to cells bound to protein or lipoprotein in biological systems, a role for specific lipoprotein receptors has been implicated. The uptake mechanisms of photosensitiser PEG conjugates have received much less attention, although fluorescence microscopy studies show that the initial intracellular distribution is limited to foci in the cytoplasm in the vicinity of the plasma membrane suggesting that endocytosis and sequestration in vesicles plays a part. One way in which uptake mechanisms may be studied is by determining the influence of temperature. In general, active (energy-dependent) uptake processes are inhibited in cells maintained at 4° C. compared to those at 37° C. Passive (energy-independent) uptake processes are much less temperature-dependent. The effect of temperature on uptake of the three photosensitisers at 1.5 µM is shown in Table 1.

be injected with a volume of 50 µl. For M-THPC, which is insoluble in water, the injection solution was prepared using a PEG400: ethanol:water vehicle (30:20:50, w/w), whilst SPC 0172 and SPC 0038B were prepared in water for injection.

Animals were sacrificed at 6, 24, 72 and 192 hours after injection of each photosensitiser. Immediately after sacrifice, blood was obtained by cardiac puncture, and centrifuged at 13,000×g for three minutes. The resulting supernatant (blood plasma) was aspirated and stored at −70° C. for subsequent analysis. The photosensitiser content of each sample was measured from the fluorescence of an extract obtained using methanol:DMSO (3:5, v:v). A 50 µl portion of each extract was transferred to a disposable fluorescence cuvette and the fluorescence determined using an excitation wavelength of 418 nm and emission wavelength of 650 nm with an eight second response setting. The assay was calibrated using stock solutions of each compound in methanol, further diluted in methanol:water (1:1, v/v) and extracted with methanol:DMSO as described above. For each photosensitiser the fluorescence yield was found to be linear up to a sample concentration of 200 nmoles per ml. The measurement protocol was designed to dilute each sample to a sufficient extent to avoid interference by endogenous chro-

TABLE 1

Effect of temperature on photosensitiser uptake by Colo26 cells

| Compound | 6 hour uptake (millions of molecules per cell) | | 24 hour uptake (millions of molecules per cell) | | Rate of uptake 6-24 h (thousands of molecules per cell per hour) | |
|---|---|---|---|---|---|---|
| | 4° C. | 37° C. | 4° C. | 37° C. | 4° C. | 37° C. |
| m-THPC | 0.82 | 79.2 | 1.33 | 208 | 28 | 7184 |
| SPC 0038B | 0.56 | 0.82 | 0.64 | 0.86 | 4 | 2 |
| SPC 0172 | 1.08 | 1.12 | 1.78 | 2.08 | 39 | 53 |

It can be seen that at 4° C. the uptake of m-THPC is inhibited by a factor of over 250. Such strong temperature dependence suggests that the uptake of this compound occurs by an active, energy-dependent process. The uptake of SPC 0038B appears to be twice as great in the cold than at 37° C. whilst that of SPC 0172 was reduced on cooling to about 75% of that at 37° C. The uptake of both PEGylated photosensitisers therefore was relatively unaffected by temperature compared to the effect with m-THPC. This suggests that SPC 0172 and SPC 0038B are taken up into tumour cells by means of an energy-independent mechanism. SPC 0172 is taken up more efficiently by tumour cells through this mechanism than SPC 0038B.

Pharmacokinetic Characteristics

An assessment of the relative pharmacokinetic characteristics has been made by comparison of the plasma concentration-time profiles for SPC 0172, SPC 0038B and m-THPC in mice bearing a subcutaneously implanted tumour.

Adult female Balb/c mice bearing the syngeneic colo26 tumour implanted subcutaneously were produced using methods previously described (Ansell et al. Lasers in Medical Science 1997, 12, 336-41). Groups of mice of weight 19-22 g were given the photosensitisers at a dose of 0.88 µmol kg$^{-1}$ (equivalent to 0.6 mg kg$^{-1}$ in the case of m-THPC) by injection into the tail vein. The solutions for injection of each compound were prepared at a concentration of 0.352 µmol ml$^{-1}$ so that a typical 20 g mouse would mophores (absorbance of samples <<0.1 at the excitation wavelength). The results obtained are presented in FIG. 5 (nano-moles per ml, n against time, t (hours)) plasma photosensitiser concentrations following injection of 0.88 nanomoles of each photosensitiser per g live weight.

Figure 5:
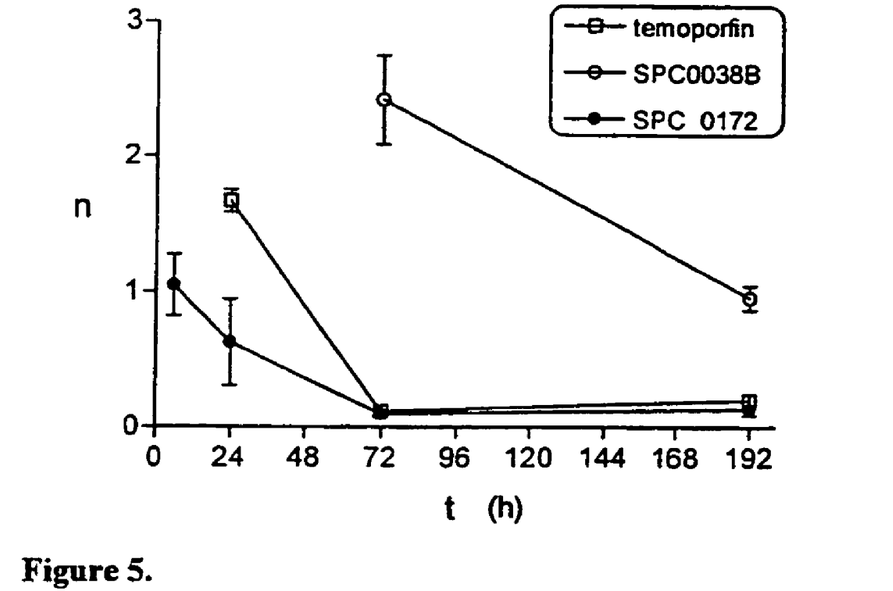

The data show that higher plasma levels of SPC 0038B occur in these mice compared to either m-THPC or SPC 0172 given at equimolar doses intravenously. It is also clear that the plasma concentrations of both m-THPC and SPC 0172 diminish to background levels more rapidly than SPC 0038B. In effect SPC 0038B persists longer and exhibits a longer terminal elimination phase from plasma compared to either SPC 0172 or m-THPC. The data indicate a fundamental difference in the plasma concentration-time profile for both PEGylated photosensitisers, with SPC 0172 showing lower absolute levels and more rapid elimination.

Figure 6:
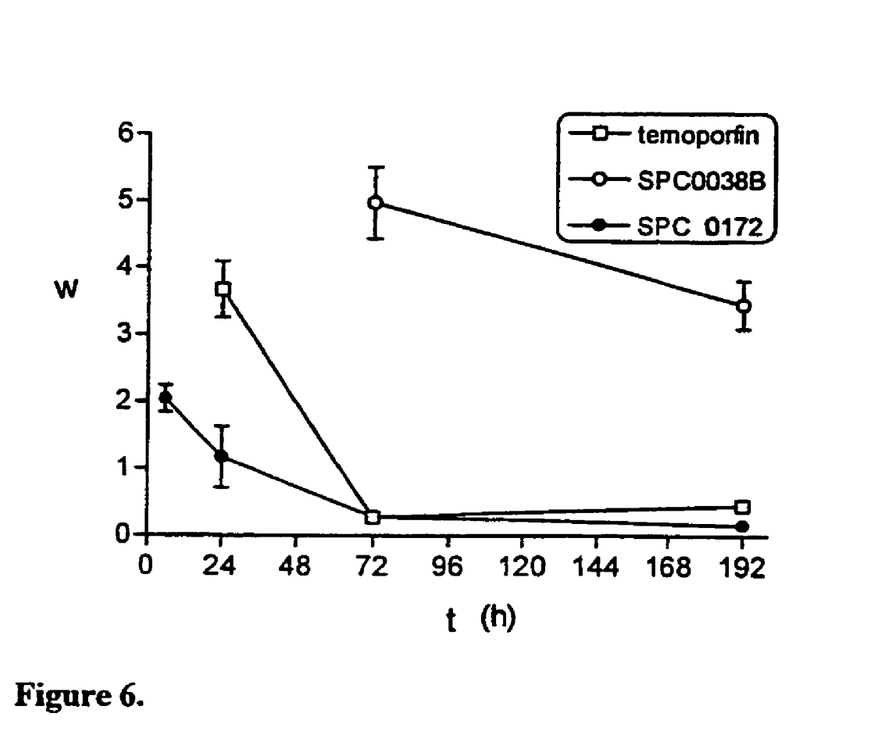

Other tissues were taken from the mice at the same timepoints as the blood samples and treated using a similar extraction and fluorescence analysis method to determine photosensitiser levels. Levels in liver mapped the same trends as seen in plasma for the three photosensitisers FIG. 6 (nano-moles per g wet weight, w against time, t (hours)) shows liver photosensitiser concentrations following injection of 0.88 nanomoles of each photosensitiser per g live weight. Once again liver levels for SPC 0038B were higher and more persistent whereas levels for SPC 0172 were lower and eliminated more quickly.

Figure 7:
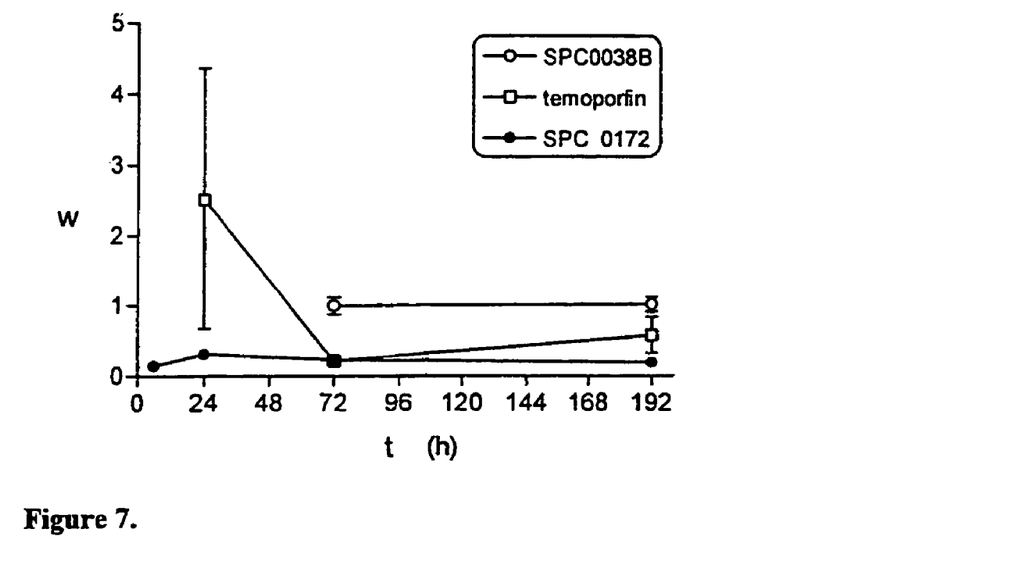

Levels in skin are presented in FIG. 7 (nano-moles per g wet weight, w against time, t (hours)), skin photosensitiser concentrations following injection of 0.88 nanomoles of each photosensitiser per g live weight. Relatively high concentrations of m-THPC occurred in skin 24 hours after administration falling to lower levels from 72 hours onwards. SPC 0172 concentrations in skin were low throughout the 6-192 hour measurement period suggesting a lower potential to cause cutaneous photosensitivity. Skin concentrations of SPC 0038B were higher than those of SPC 0172 or m-THPC between 72 and 192 hours suggesting a higher potential to cause cutaneous photosensitivity during this period.

The selectivity for tumour specific tissue distribution was also evaluated in this work. Tissue selectivity was evaluated as the tumour:muscle concentration ratio over the duration of the observation period (4-192 hours post-administration). This ratio provided a direct measure of the normal tissue to tumour tissue differential in concentrations and allows selection of an optimal treatment time for PDT that minimises the potential to cause collateral damage of normal tissues. The results obtained are presented in FIG. 8 (Tumour:muscle ratio, r against time, t (hours)), Tumour:muscle concentration ratio of the three photosensitisers.

Figure 8:
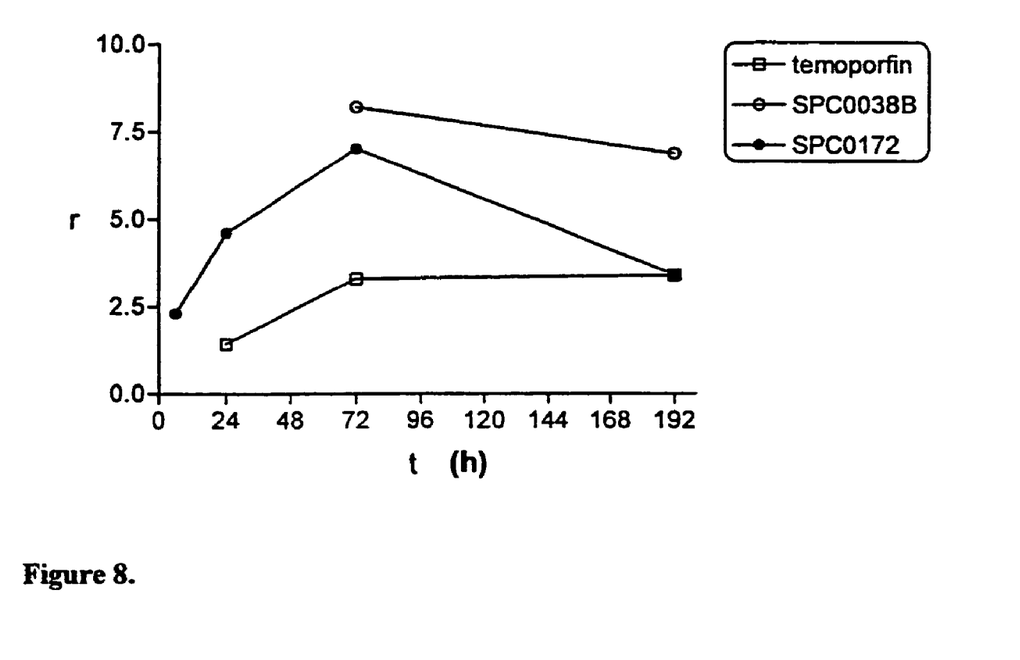

The results indicate an optimal tumour:muscle concentration ratio for SPC 0172, and hence tumour PDT, occurs at 72 hours post-administration. The ratio value of about 7.5 with SPC 0172 was similar to that that obtained with SPC 0038B at the same timepoint and 2-3 fold higher than that observed with m-THPC. Both PEGylated photosensitisers therefore exhibit improved tumour targeting in comparison to m-THPC. In comparison to SPC 0172, the favourable tumour: muscle ratio for SPC 0038B does not decline as rapidly beyond 72 hours suggesting a broader window for tumour PDT but also the less attractive feature of persistent PDT bioactivity in the target tissue. SPC 0172 exhibits the most appropriate profile for tumour PDT of these two PEGylated photosensitisers with a single optimum at 72 hours and low skin levels suggesting a reduced potential to cause cutaneous photosensitivity.

Published work (Grahn et al, Proc. SPIE 1997, 3191, 180-6) with SPC 0038B in this model support the observation that this photosensitiser is eliminated more slowly than m-THPC.

This work also showed that SPC 0038B concentrations measured in muscle peaked at or before 72 hours after injection whilst those in tumour peaked between 72 and 144 hours, after which they declined. An optimal drug-light treatment interval for tumour PDT specific tissue necrosis later than 72 hours post-administration was therefore indicated. Allied measurements of tumour bioactivity showed sustained PDT tumour necrosis from SPC 0038B occurred for PDT treatment times ranging from 4-15 days. This report also confirms the persistence of liver concentrations of SPC 0038B. These data further illustrate a phenomenon of persistent tumour levels and sustained potential for PDT-mediated tumour necrosis with SPC 0038B that are sub-optimal characteristics of an ideal PDT agent.

Cutaneous Photosensitivity

Cutaneous photosensitivity was determined in adult female Balb/c mice, held under standard conditions and allowed access to food and water ad libitum. Groups of mice of weight 19-22 g were given the photosensitisers at a dose of 0.88 µmol kg$^{-1}$ by injection into the tail vein. The solutions for injection of each compound were prepared at a concentration of 0.352 µmol ml$^{-1}$ so that a typical 20 g mouse would be injected with a volume of 50 µl. Each mouse was weighed immediately before injection and the injected volume adjusted to give the correct dose. For m-THPC the injection solution was prepared using the standard PEG400: ethanol:water vehicle, whilst SPC 0172 and SPC 0038B were prepared in water for injection.

At 24 or 72 hours after photosensitiser injection one ear of each mouse was irradiated with full-spectrum xenon light from a 1 KW clinical photo-irradiator (Model UV-90, Applied Photophysics, London). The light was delivered to the ear using a 7 mm diameter light guide (Serial SU3) placed lightly against the ear. The light dose given was 40 Joules per cm$^2$, which was achieved by exposing the ear for 63 seconds to 245 mW of light from the light guide having a contact area of 0.384 cm$^2$. The light guide filtered infra-red and ultra-violet light, so as to minimise heating of the ear and damage resulting from ultra-violet light irradiation.

Animals treated with light at the 24 or 72 hour drug-light intervals were killed at 48 or 24 hours respectively after irradiation of the ears. The oedema of the irradiated and control ears was assessed by measuring ear thickness. The thickness of the ear was measured at three sites on the upper third of the ear using a fixed-force micrometer with a vernier-interpolated resolution of 2 µm and an accuracy of 10 µm (Neill instruments).

The results indicate that ear swelling or thickness, as a surrogate endpoint for cutaneous photosensitivity, is lower with SPC 0172 than with SPC 0038B or m-THPC following light irradiation either at 24 or 72 hours after photosensitiser administration (Table 2). SPC 0038B exhibited superiority over m-THPC to cause less photosensitivity at the 24 hour drug-light interval but this difference was negated even reversed by the 72 hour drug-light interval. These observations match the trends in skin concentrations of these photosensitisers noted earlier. The indication therefore is that SPC 0172 is superior to SPC 0038B or m-THPC in terms of potential to cause cutaneous photosensitivity.

TABLE 2

Differences in ear thickness (irradiated-control) in µm for mice injected with 0.88 µmol kg$^{-1}$ of each photosensitiser 24 or 72 hours before light irradiation.

| Photosensitiser | 24 h drug-light interval | | | 72 h drug-light interval | | |
|---|---|---|---|---|---|---|
| | Mean | SEM [1,2] | N | Mean | SEM [1,2] | N |
| SPC 0038B | 25 | 7 (16 to 38) | 3 | 4 | 6 (−2 to 15) | 3 |
| SPC 0172 | 2 | (22; −18) | 2 | 0 | (8; −8) | 2 |
| m-THPC | 41 | 25 (8 to 90) | 3 | 2 | 7 (−12 to 13) | 3 |

[1] Standard error of mean.
[2] Range or individual values provided in parentheses.

Tumour PDT Activity

Information on the tumour PDT activity have been obtained in the aforementioned mouse model bearing the syngeneic colo26 tumour implanted subcutaneously at the top of the left hind leg (approximately 1 cm lateral to the spine). The tumours were used after 12 to 16 days when they had reached an average diameter of 8 to 10 mm. For drug injection and irradiation animals were sedated with Hypnorm diluted in water (1:3).

SPC 0172 demonstrated tumour necrosis at 1 day after drug injection which increased in extent at two days post-injection (Table 3). The effect observed at two days post-injection comprised full tumour necrosis, an effect equivalent to that observed with m-THPC at half the dose in the same timescale. Examination of the treated sites with SPC 0172 suggested that tumour necrosis was accompanied by only limited damage of the surrounding skin and underlying muscle, particularly at the two day drug-light interval.

Further experiments using the same dose of SPC 0172 and a light dose of 20 J cm$^{-2}$ were carried out at a range of drug-light intervals. Full thickness tumour damage was observed at all drug-light intervals up to 72 hours.

Comparative data on SPC 0038B at its optimal drug-light interval of 72 hours in this model show 10-20 fold less potency on a dose level and degree of tumour necrosis basis in comparison to SPC 0172 and m-THPC.

The results suggest that the in-vivo potency of SPC 0172 as a tumour PDT agent is similar to that of m-THPC at its optimal dose (0.88 µmol kg$^{-1}$) whereas SPC 0038B is somewhat less potent.

TABLE 3

Tumour necrosis induced in the mouse implanted colorectal tumour model by the 3 photosensitisers

| Compound | Drug Dose (µmol kg$^{-1}$) | Drug-light interval (hours) | Light applied at 652 nm (J cm$^{-1}$) at 100 mW cm$^{-1}$ | Biological effect (mm of tumour necrosis) |
|---|---|---|---|---|
| SPC 0172 | 1.76 | 24 | 20 | 3.8 ± 1.3 |
| SPC 0172 | 1.76 | 48 | 10 | Full thickness (>6 mm) |
| SPC 0038B | 4.4 | 72 | 5 | 3.3 ± 0.7 [1] |
| m-THPC | 0.88 | 24 | 5 | 5.8 ± 0.4 |
| m-THPC | 0.88 | 48 | 5 | 5.6 ± 0.8 |

[1] Taken from Grahn et al Proc. SPIE 1997, 3191, 180-6.

CONCLUSION

In summary, PEGylated photosensitisers exhibit improved water solubility compared to the parent photosensitiser m-THPC making them far more pharmaceutically acceptable for parenteral administration. They are taken up by tumour cells in a different energy-independent mechanism compared to m-THPC in which SPC 0172 is more efficient than SPC 0038B. Improved tumour targeting over m-THPC was achieved by these PEGylated molecules with SPC 0172 showing a superior pharmacokinetic profile compared to SPC 0038B with a peak in tumour: normal tissue ratio within 72 hours of administration and more rapid elimination from the tissues and plasma. A lower potential to cause cutaneous photosensitivity was evident with SPC 0172 over SPC 0038B or m-THPC and a similar potency to m-THPC for tumour necrosis following PDT by SPC 0172 was shown whereas SPC 0038B was less active. It is therefore apparent that carbamate-linked PEGylated photosensitisers as evidenced by SPC 0172 are more ideal tumour PDT agents than triazine-linked PEGylated photosensitisers as evidenced by SPC 0038B, and possess improved features in comparison to m-THPC.

The invention claimed is:
1. The compounds selected from:
7,8-Dihydro-5, 10, 15,20-tetrakis(3-hydroxyphenyl)prophyrin derivatised with ω-methoxy polyethylene glycol (average MW=2000) via biscarbamate linkages derived from hexane-1,6-diisocyanate;
7,8,17,18-Tetrahydro-5, 10, 15,20-tetrakis(3-hydroxyphenyl)prophyrin derivatised with ω-methoxy poly(ethylene glycol) (average MW=2000) via bis carbamate linkages derived from hexane-1,6-diisocyanate;
7,8-Dihydro-5, 10, 15,20-tetrakis(3-hydroxyphenyl)prophyrin derivatised with ω-methoxy poly(ethylene glycol) (average MW=5000) via bis carbamate linkages derived from hexane-1,6-diisocyanate; and
7,8,17,18-Tetrahydro-5, 10, 15,20-tetrakis(3-hydroxyphenyl) prophyrin derivatised with ω-methoxy poly(ethylene glycol) (average MW=5000) via bis carbamate linkages derived from hexane-1,6-diisocyanate.

* * * * *